US00PP21547P2

(12) United States Plant Patent
Kent

(10) Patent No.: US PP21,547 P2
(45) Date of Patent: Nov. 30, 2010

(54) ***GUZMANIA* PLANT NAMED 'CERISE'**
(50) Latin Name: ***Guzmania* hybrid**
Varietal Denomination: Cerise

(76) Inventor: Jeffrey Kent, P.O. Box 2166, Vista, CA (US) 92085-2166

( * ) Notice: Subject to any disclaimer, the term of this patent is extended or adjusted under 35 U.S.C. 154(b) by 0 days.

(21) Appl. No.: 12/460,377

(22) Filed: Jul. 18, 2009

(51) Int. Cl.
*A01H 5/00* (2006.01)

(52) U.S. Cl. ..... Plt./371
(58) Field of Classification Search ..... Plt./371

See application file for complete search history.

*Primary Examiner*—Kent L Bell

(57) ABSTRACT

A new and distinct *Guzmania* cultivar named 'Cerise' is disclosed, characterized by a compact plant habit, and unique bright red-purple bracts.

1 Drawing Sheet

Figure 1:
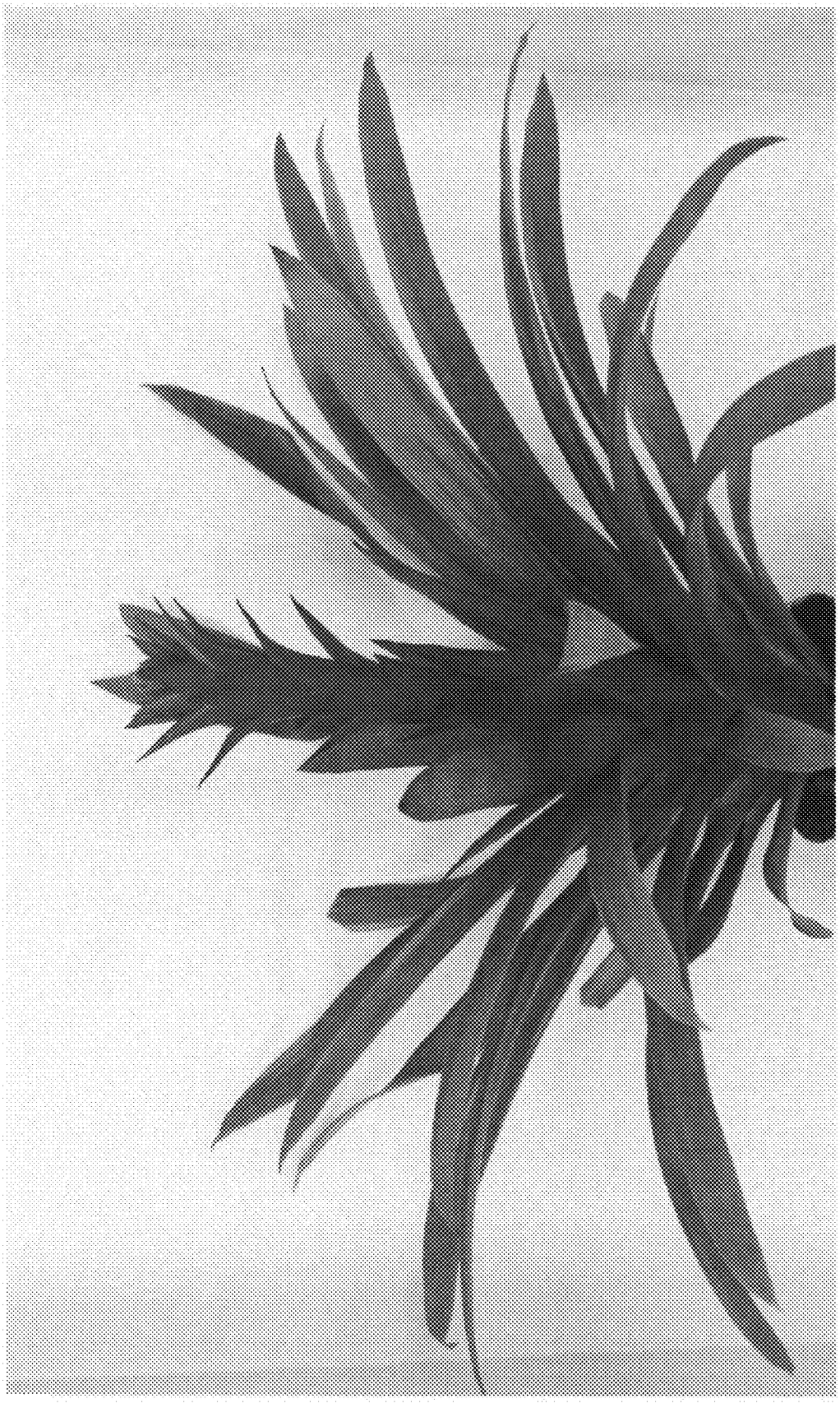

Latin name of the genus and species: *Guzmania* hybrid.
Variety denomination: 'Cerise'.

BACKGROUND OF THE INVENTION

The new cultivar is a product of a planned breeding program. The new variety originated from a cross pollination of the seed parent, an unnamed proprietary variety of *Guzmania* hybrid with the unnamed pollen parent *Guzmania lingulata*, directed by the inventor in October of 2004.

'Cerise' was discovered by the inventor, Rolf Kurt Zornig, in October 2006 in Campinas, Brazil in a group of seedlings resulting from the 2004 crossing.

Asexual reproduction of the new cultivar 'Cerise' was first performed in Campinas, Brazil by tissue culture in July 2007. 'Cerise' has since produced several generations by micropropagation and has shown that the unique features of this cultivar are stable and reproduced true to type.

SUMMARY OF THE INVENTION

The cultivar 'Cerise' has not been observed under all possible environmental conditions.

The phenotype may vary somewhat with variations in environment such as temperature, day length, and light intensity, without, however, any variance in genotype.

The following traits have been repeatedly observed and are determined to be the unique characteristics of 'Cerise' These characteristics in combination distinguish 'Cerise' as a new and distinct *Guzmania* cultivar:

1. Compact plant shape.
2. Long inflorescence.
3. Purple-Red inflorescence color.
4. Suitability as an indoor pot plant.

PARENTAL COMPARISON

Plants of the new cultivar 'Cerise' are similar to both parent varieties in most horticultural characteristics. However, 'Cerise' differs from both the seed and pollen parents in having a more compact plant shape and longer inflorescence.

COMMERCIAL COMPARISON

'Cerise' can be compared to the patented commercial variety *Guzmania* 'Deplakar,' U.S. Plant Pat. No. 13,754. Plants of 'Deplakar' are similar to plants of 'Cerise' in most horticultural characteristics, however, 'Cerise' has shorter, narrow foliage, scape and terminal bracts more yellow than orange-yellow in color.

'Cerise' can be compared to the unpatented commercial variety *Guzmania* 'Marjan' Plants of 'Marjan' are similar to plants of 'Cerise' in most horticultural characteristics, however, 'Cerise' has a wider inflorescence, and a shorter overall plant height than 'Marjan'.

BRIEF DESCRIPTION OF THE PHOTOGRAPH

The accompanying photograph in FIG. 1 illustrates in full color a typical plant of 'Cerise' grown in a greenhouse in Florida. This plant is approximately 1 year old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Cerise' plants grown in a climate controlled greenhouse in Miami, Fla. Temperatures ranged from 20° C. to 28° C. night and day. No artificial light, photoperiodic treatments or chemical treatments were given to the plants. Measurements and numerical values represent averages of typical plant types.

Botanical classification: *Guzmania hybrid.* cultivar 'Cerise'.
Age of the plant described: Approximately 1 year.
Container size of the plant described: 6 inch.

PLANT

Growth habit: Upright, arching, forming compact rosettes around a single axis. Single, straight, upright inflorescence arising from the center of plant.

Height: Approximately 45 cm in a 6 inch pot, measured from the soil level of the pot.

Plant spread: Approximately 85 cm in a 6 inch pot.

Normal pot size: 6" and larger pots.
Growth rate: Rapid.
Branching characteristics: Upright, non-branching.
Number of leaves per stem: Approximately 40.
Stem length: Approximately 10 cm.
Stem width: Approximately 12 cm.
Stem color: Near RHS Red-Purple 59B with stripes near Greyed-Purple 187A and near Yellow-Green 147D.
Stem texture: Smooth.
Age of plant described: Approximately 1 year.

FOLIAGE

Leaf:

*Arrangement.*—Whorled, single occurring basal rosettes.
*Average length.*—Approximately 35 to 40 cm.
*Average width.*—Approximately 2 cm.
*Shape of blade.*—Ligulate.
*Aspect.*—Recurved.
*Apex.*—Apiculate.
*Base.*—Sheathing. Sheath length: Average 4.0 cm. Sheath width: Average 4.0 cm. Sheath color: Near RHS Yellow-Green 147D with flushing near Red-Purple 59B and stripes near Greyed-Purple 187A.
*Margin.*—Entire.
*Texture of top surface.*—Smooth, slightly glossy.
*Texture of bottom surface.*—Smooth, slightly glossy.
*Color.*—Young foliage upper side: Coloration divided into 2 sections: ⅔ leaf blade closest to apex: Near RHS Green 137B, very thin margin of color near Red-Purple 60A. ⅓ leaf blade closest to base: Near RHS Red-Purple 60A. Young foliage under side: Coloration divided into 2 sections: ⅔ leaf blade closest to apex: Near RHS Green 137C, very thin margin of color near Red-Purple 61B. ⅓ leaf blade closest to base: Near RHS Red-Purple 61B. Mature foliage upper side: Coloration divided into 2 sections: ⅔ leaf blade closest to apex: Near RHS Green 137B. ⅓ leaf blade closest to base: Near RHS Red-Purple 59C. Mature foliage under side: Coloration divided into 2 sections: ⅔ leaf blade closest to apex: Near RHS Green 137B. ⅓ leaf blade closest to base: Near RHS Red-Purple 59C.
*Venation.*—Type: Parallel. Venation coloration: Indistinguishable from foliage coloration.

Petiole: Not present, sessile.

INFLORESCENCE

General description: Simple spike(scape) consisting of many bracts only. No individual flowers are visible. Spike emerges from the centre of the rosette. Inflorescence is formed by conspicuous bracts.

*Inflorescence height, excluding scape.*—Approximately 20 cm.
*Inflorescence width.*—Approximately 12 cm.

Scape:

*Length.*—Approximately 15 cm.
*Width.*—Approximately 3.5 cm.
*Aspect.*—Very straight, Approximately 80° angle to rosette.
*Strength.*—Very strong.
*Color.*—Near RHS Red-Purple 58A.

Bracts:

*Scape/lowermost bracts.*—Shape: Ligulate. Length: Approximately 12 cm, excluding sheath. Width: Approximately 3.1 cm. Quantity: Average 6. Tip: Acute. Base: Sheathed. Sheath length: Approximately 5 cm. Sheath width: Approximately 4.5 cm. Sheath color: Near RHS Red-Purple 58A.

Margin: Entire. Color Upperside: Near RHS Red-Purple 58A, up to ⅔ from base. ⅓ near apex, near RHS Green 137A with flusing near Red-Purple 59A. Color Underside: Near RHS Red-Purple 58A, up to ⅔ from base. ⅓ near apex, near RHS Greyed-Purple 187B.

*Terminal bracts.*—Shape: Ligulate. Length: Approximately 9 cm, excluding sheath. Width: Approximately 3 cm. Quantity: Average 17 to 18. Tip: Acute. Base: Sheathed. Sheath length: Approximately 4 cm. Sheath width: Approximately 4 cm. Sheath color: Near RHS Red-Purple 58A. Margin: Entire. Coloration Terminal Bracts: Upperside: Near RHS Red-Purple 60A. Underside: Near RHS Red-Purple 60A.

OTHER CHARACTERISTICS

Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed.
Fruit/seed production: Not observed.

What is claimed is:

1. A new and distinct cultivar of *Guzmania* plant named 'Cerise' as herein illustrated and described.

* * * * *